United States Patent
Kriesel et al.

(10) Patent No.: US 11,142,373 B1
(45) Date of Patent: *Oct. 12, 2021

(54) STABILIZED COSMETIC TRAY DISPLAY

(71) Applicant: Tak Logic LLC, Ettrick, WI (US)

(72) Inventors: Matthew Wayne Kriesel, Melrose, WI (US); Troy Bradley Goodenough, Mindoro, WI (US)

(73) Assignee: Tak Logic, LLC, Ettrick, WI (US)

( * ) Notice: Subject to any disclaimer, the term of this patent is extended or adjusted under 35 U.S.C. 154(b) by 141 days.

This patent is subject to a terminal disclaimer.

(21) Appl. No.: 15/732,729

(22) Filed: Dec. 22, 2017

Related U.S. Application Data

(63) Continuation-in-part of application No. 15/731,815, filed on Aug. 7, 2017, which is a continuation-in-part of application No. 14/999,722, filed on Jun. 20, 2016, now Pat. No. 10,807,767.

(60) Provisional application No. 62/231,004, filed on Jun. 22, 2015.

(51) Int. Cl.
| | |
|---|---|
| *B65D 25/04* | (2006.01) |
| *B05D 1/02* | (2006.01) |
| *B65D 33/06* | (2006.01) |
| *A61B 50/33* | (2016.01) |
| *A01K 97/06* | (2006.01) |
| *A61B 50/30* | (2016.01) |
| *A61B 50/00* | (2016.01) |
| *C08G 18/10* | (2006.01) |
| *C08G 18/36* | (2006.01) |
| *C08G 18/48* | (2006.01) |

(52) U.S. Cl.
CPC .............. *B65D 25/04* (2013.01); *A01K 97/06* (2013.01); *A61B 50/33* (2016.02); *B05D 1/02* (2013.01); *B65D 33/06* (2013.01); *A61B 2050/002* (2016.02); *A61B 2050/3008* (2016.02); *C08G 18/10* (2013.01); *C08G 18/36* (2013.01); *C08G 18/4825* (2013.01); *C08G 18/4829* (2013.01)

(58) Field of Classification Search
CPC ........ B65D 25/04; B65D 33/06; A01K 97/06; A61B 50/33; A61B 2050/3008; A61B 2050/002; B05D 1/02; C08G 18/4829; C08G 18/36; C08G 18/10; C08G 18/4825
See application file for complete search history.

(56) References Cited

U.S. PATENT DOCUMENTS

| | | | |
|---|---|---|---|
| 3,507,071 A | 4/1970 | Bryson | |
| 5,677,413 A | 10/1997 | Barksby et al. | |
| 5,864,001 A | 1/1999 | Masse et al. | |
| 6,588,511 B1 | 7/2003 | Kriesel et al. | |
| 6,673,409 B1 * | 1/2004 | Wheatley | B60R 7/02 296/97.3 |
| 6,896,065 B2 | 5/2005 | Kriesel et al. | |
| 7,041,719 B2 | 5/2006 | Kriesel et al. | |
| 7,125,602 B2 | 10/2006 | Wheatley | |
| 7,252,867 B2 | 8/2007 | Wheatley | |
| 7,910,188 B2 | 3/2011 | Wheatley | |
| 7,923,088 B2 | 4/2011 | Wheatley | |
| 8,110,269 B2 | 2/2012 | Wheatley | |
| 8,110,270 B2 | 2/2012 | Wheatley | |
| 8,302,213 B2 | 11/2012 | Kriesel | |
| 9,974,342 B1 | 5/2018 | Kriesel | |
| D880,950 S | 4/2020 | Kriesel et al. | |
| 10,681,830 B1 | 6/2020 | Goodenough | |
| 10,717,582 B1 | 7/2020 | Goodenough | |
| 10,807,767 B1 | 10/2020 | Kriesel et al. | |
| D902,584 S | 11/2020 | Kriesel et al. | |
| 10,914,087 B1 | 2/2021 | Kriesel et al. | |
| 2004/0191446 A1 | 9/2004 | Kriesel | |
| 2004/0200623 A1 | 10/2004 | Kriesel | |
| 2005/0019587 A1 * | 1/2005 | Luhmann | C08G 18/4812 428/423.1 |
| 2005/0027091 A1 * | 2/2005 | Luhmann | C08G 18/227 528/44 |
| 2006/0272367 A1 | 12/2006 | Kriesel | |
| 2006/0287147 A1 | 12/2006 | Kriesel | |
| 2007/0254152 A1 * | 11/2007 | Schumann | C08G 18/758 428/355 N |
| 2008/0005929 A1 | 1/2008 | Hardy et al. | |
| 2008/0026658 A1 | 1/2008 | Kriesel | |
| 2008/0250729 A1 | 10/2008 | Kriesel | |
| 2009/0042676 A1 | 2/2009 | Kriesel | |
| 2010/0170139 A1 | 7/2010 | Zhou | |
| 2012/0222457 A1 | 9/2012 | Kriesel et al. | |
| 2013/0288060 A1 | 10/2013 | Pind et al. | |
| 2015/0053583 A1 | 2/2015 | McCormick et al. | |

\* cited by examiner

*Primary Examiner* — Rabon A Sergent

(74) *Attorney, Agent, or Firm* — M. Paul Hendrickson; Bryan R. Rosiejka

(57) ABSTRACT

Stabilizing cosmetic trays adapted to restrain cosmetic items in a steadfast emplaced position are provided by equipping the cosmetic tray beds with a cohesive and adhesive thermoset overlay typically provided by overlaying a bed of the cosmetic tray therewith. The overlay adhesively restrains emplaced cosmetic items until physically removed by force from the overlay by the cosmetic user.

34 Claims, 3 Drawing Sheets

STABILIZED COSMETIC TRAY DISPLAY

CROSS-REFERENCE TO RELATED APPLICATIONS

This application is a Continuation-in-part of U.S. Non-provisional patent application Ser. No. 15/731,815 filed Aug. 7, 2017, which is a U.S. Non-provisional Continuation-in-part of U.S. patent application Ser. No. 14/999,722 filed Jun. 20, 2016, which is a U.S. Non-provisional of U.S. Provisional Patent Application No. 62/231,004 filed Jun. 22, 2015, all of which applications are incorporated by reference in their entirety herein.

FIELD OF INVENTION

The present invention relates to totable cosmetic devices, and more particularly to cosmetic containers and/or cosmetic trays.

BACKGROUND OF THE INVENTION

Cosmeticians, cosmetic sales persons and household cosmetic users customarily use cosmetic trays for display or simply to place cosmetics in an accessible and orderly manner. A common problem arises by an inability to maintain the trayed cosmetics in an orderly and presentable condition. Unfortunately, many of the cosmetic containers are irregular in shape and, when left open for accessible tray use, make it most difficult to restrain cosmetic items in an orderly and presentable condition, especially under disruptive usage (e.g., dropping, jarring, etc.), which can easily disarrange or ruin an aesthetic tray display. A host of restraining systems designed to maintain cosmetics in a presentable condition have been proposed. Such proposals involve designing a mating cavity or impression which maintains a matching cosmetic item in a housed position. This involves countless different types of cavities to match a host of different cosmetic container shapes. Another system involves affixing magnets to the cosmetic tray bed to retain ferrous metal containing cosmetic items in a steadfast position. However, since most cosmetics are customarily contained in plastic and glass containers, the magnets are generally unfit to restrain such non-metal containers. Still other restraining systems, such as physical restraining straps, hooks and loop fasteners, have seen limited application usage.

There exists a need for a cosmetic display tray to restrain cosmetic items in an open, aesthetic and orderly manner while also providing a readily accessible cosmetic display tray for the cosmetic user. Household consumers of cosmetics, as well as cosmetic wholesalers, retailers, door-to-door sales person, etc., would greatly benefit if there existed a reliable tray system which allowed cosmetics to be effectively toted or displayed without undue concern as to dislodgement, jarring, dropping or otherwise displacing the cosmetic items from their original stowed position.

Reportedly, there exists more than a million worldwide door-to-door sales persons having a need to maintain cosmetics in a transportable and presentable tray display format. Extraordinary and expensively designed cosmetic display trays, as well as cosmetic containers, have been specially designed to maintain the cosmetics in an orderly and aesthetic display fashion. Often, a hasty placement or removal of a cosmetic item from a tray will cause many of the other openly displayed cosmetics to fall into disarray or become damaged. This disrupts the sale effort and creates an unsightly display, often requiring a tedious effort to reorganize the display, all of which can substantially hinder and adversely affect the sale effort. The consuming public would greatly benefit if there existed a totable cosmetic tray which would restrain a cosmetic item where it was placed until ultimately needed by the cosmetic user.

BRIEF SUMMARY OF THE INVENTION

The age old problem of restraining cosmetic items in an orderly, stabilized, presentable and openly accessible position in a totable tray form has been effectively overcome by overlaying a suitable supportive member (e.g., a bed of a cosmetic display tray) with a polymeric overlay having sufficient adhesiveness to adhesively adhere and restrain a host of cosmetic items at an openly presentable position, while also allowing an orderly retrieval of selected cosmetic items by an outwardly pulling force sufficient to overcome the adhesive attraction between the cosmetic item and the polymeric overlay. The polymeric overlay also possesses sufficient internal cohesiveness so as to cleanly release itself from the removed cosmetic item without leaving any polymeric residue upon the released cosmetic item.

A particularly effective cohesive and adhesive polymeric overlay comprises a thermoset polymeric material generally characterized as possessing an adhesive release strength of at least 300 grams force per square centimeter ($g_f/cm^2$) and sufficient structural integrity so as to remain substantially intact after the adhesive separation from the cosmetic item. The most effective polymeric overlays include thermoset viscoelastomeric polymerizates formulated with a sufficient amount of thermosetting cross-linking precursors and plasticizers to provide the desired level of adhesion release strength for effective use herein.

Certain of these thermoset polymerizates characteristically possess adhesive thermoset bonding properties, which allows for a cured thermoset overlay upon in situ thermosetting to become tenaciously bonded to a suitable flexible base or a rigid supportive base. Alternatively, the cohesive and adhesive characteristics of the overlay polymerizate will permit its use as a removable inlay or bed liner. Although the thermoset polymerizate has a tendency to adhesively attract dust and other external airborne contaminants resulting in an adhesive loss, the overlay adhesiveness may be easily restored by customary cleansing techniques, such as by washing (e.g., manual or automatic dishwashing). If desired, a temporary protective covering may be used to protect the polymerizate against dust collection. In addition to cosmetic items, conventional health and beauty devices such as nail files and clippers, combs, and other cosmetic grooming aids may be effectively stowed, along with the other cosmetic beauty aids. The open tray stowage provided by conventional cosmetic trays tends to create an ideal pathogenic growth environment. However, due to its exceptional antipathogenic properties, the thermoset polymerizate overlay of the invention effectively maintains a healthy and sterile environment for the stowed cosmetics.

BRIEF DESCRIPTIONS OF THE FIGURES

DETAILED DESCRIPTION OF THE INVENTION

Figure 1:
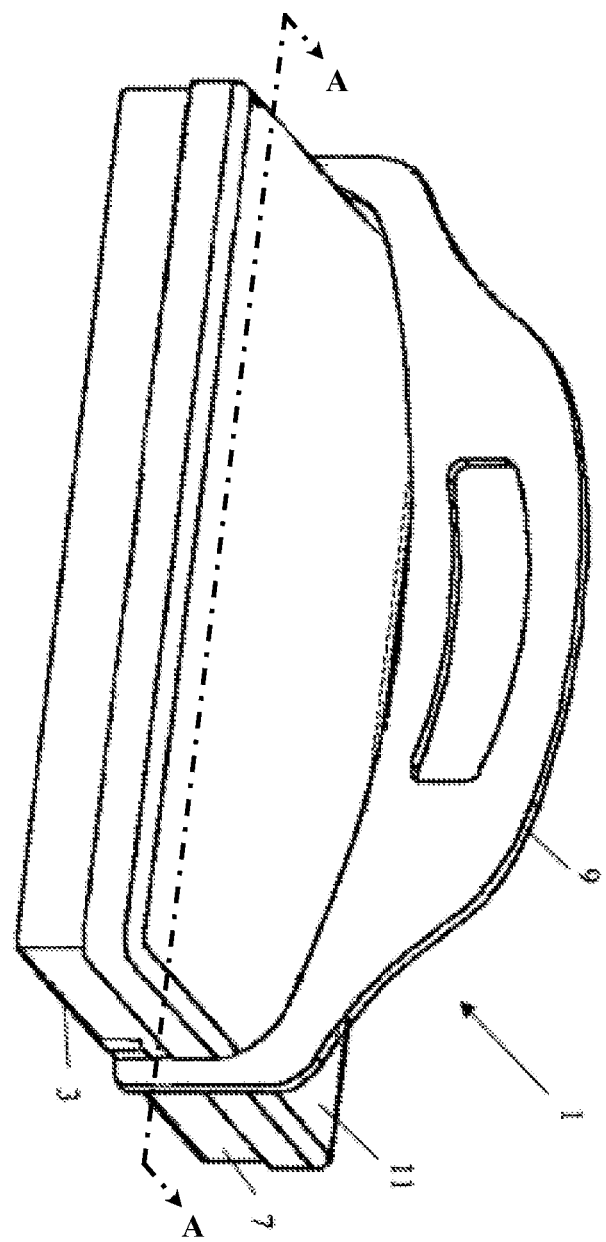
FIG. 1 is a perspective view showing a totable cosmetic display tray of this invention equipped with an adhesive thermoset polymerizate overlay.
Figure 2:
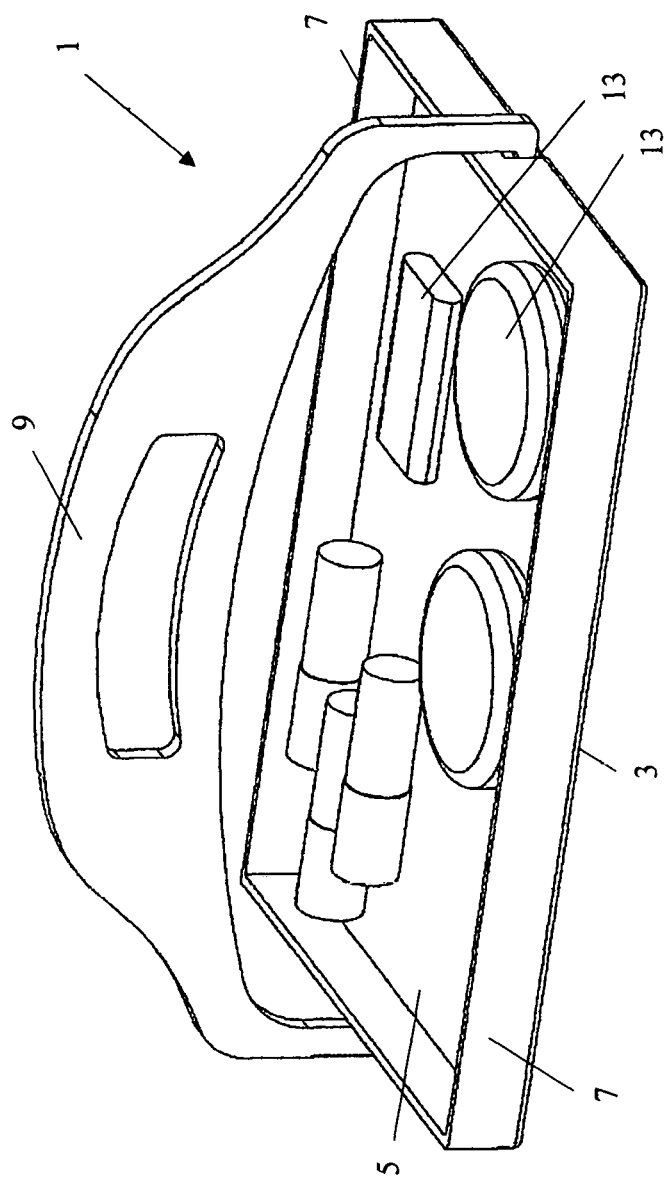
FIG. 2 is a perspective view of the cosmetic display tray of FIG. 1 wherein the cover has been removed, and wherein the display tray is equipped with an array of cosmetic items adhesively engaged to the overlay.
Figure 3:
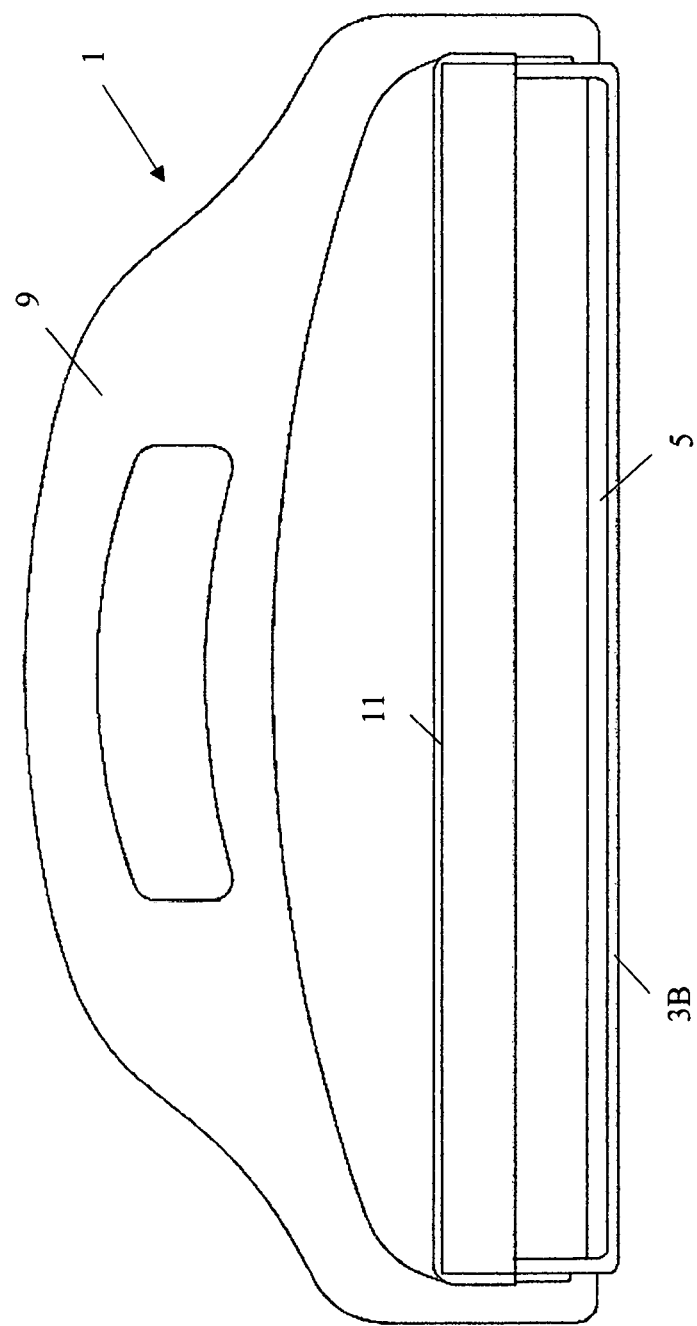
FIG. 3 is a cross-sectional view of the cosmetic display tray of FIG. 1 taken along line A-A.

With reference to FIGS. 1-3, the present invention provides a cosmetic display tray 1 comprising a supportive tray base 3 and a thermoset polymerizate overlay 5 bonded (by adhesion or by thermoset bonding) to the tray bed 3B. If desired, the cosmetic display tray 1 may be provided in a totable tray form suitably equipped with side rails 7, a handle 9 (which may be optionally removable) and a removable top cover 11. Since the thermoset overlay 5 effectively adhesively restrains items 13 emplaced thereupon in a steadfast restrained position, conventional compartmentalized tray sections, side rails, covers or other confining systems are generally unneeded.

The cohesive and adhesive thermoset overlay 5 is generally characterized as having sufficient adhesiveness to adhesively engage and restrain a cosmetic item 13 at an emplaced stowable position. The restrained item 13 will remain in the originally restrained position until item 13 is physically removed therefrom, typically by applying an outward pulling force sufficient to overcome the adhesive attraction. A suitable test for determining the adhesive efficacy of an overlay 5 includes ascertaining the particular adhesion release strength value for any given adhesive thermoset polymerizate overlay 5. The adhesion release strength testing procedure and testing apparatus for its determination is disclosed in greater detail in the aforementioned co-pending U.S. Non-provisional patent application Ser. No. 15/731,815.

The thermoset polymerizate, when used as an overlay 5, should possess sufficient adhesive attraction towards the cosmetic item 13 to restrain it at an orderly restrained position. From a user's viewpoint, an excessively high adhesion release strength value would typically result in more difficulty for the cosmetic user to remove a cosmetic item 13 from the overlay 5. Accordingly, when the adhesion release strength value increases, the force needed to remove the cosmetic item 13 from the overlay 5 will correspondingly increase. At relatively higher adhesion release strength values (e.g., greater than 1,200 $g_f/cm^2$), it becomes more strenuous to remove an item 13. Excessive adhesive attraction forces can make it necessary for the cosmetic user to hold the tray 1 with one hand while removing the cosmetic item 13 therefrom with the other hand. Since it is desirable to provide sufficient tack or adhesiveness to restrain the cosmetic item 13 at a restrained position while making it relatively easy for the user to remove the item 13 with one hand (i.e., without also holding the tray 1 with the other hand), the adhesion release strength for most common usages will typically range from about 400 $g_f/cm^2$ to about 800 $g_f/cm^2$.

The most useful overlays 5 generally include those thermoset polymerizates meeting the aforementioned adhesion release strength values, coupled with an innate ability to cohesively retain structural integrity upon the overlay's 5 separation from the cosmetic item 13 without leaving more than a miniscule amount of polymerizate residue upon the separated item 13. The thermoset overlays 5 may be typically bonded to the cosmetic tray bed 3B simply by physical adhesive bonding (relying upon the adhesiveness of the thermoset polymerizate for bonding) or alternatively by curing a thermosetting reaction product precursor upon the bed 3B to provide a thermoset polymerizate overlay 5 bonded thereto.

A particularly effective reaction media for preparing the cohesive and adhesive overlay 5 involves preparing a viscoelastomeric thermoset overlay 5 which may be suitably derived from a thermosetting reaction media containing 25% to less than 52% by weight plasticizer having an epoxidized triglyceride plasticizer content of less than 50%, from about 35% by weight to about 55% by weight of straight chain linking diols and cross-linking polyols, and from about 4% to 7% by weight of a polyurethane precursor (e.g., a polyol reacted with an isocyanate). The content and the type of polyols have been found to have a pronounced effect upon imparting the necessary thermoset polymeric infrastructure for preparing the desired unique cohesive and adhesive attributes of the stabilizing viscoelastomeric thermoset overlay 5 herein. An appropriate balance between straight chain producing diols and cross-linking polyols (e.g., triol) provides a reaction media for preparing a polyurethane reaction product (i.e., thermoset viscoelastomer) possessing especially unique cohesive and adhesive compositional properties for use as a stabilizing adhesive overlay 5 herein. A reaction product overlay 5 having an adhesion strength of less than 300 $g_f/cm^2$ will generally fail to provide a sufficient adhesive strength to restrain the cosmetic item 13 in a stabilized and stowable form. Adhesiveness of the stabilizing overlay 5 depends partly upon a proper polyol balance within the thermosetting reaction media. It has been found that when the weight ratio of diols to triols in the presence of an effective amount of plasticizer within the reaction media falls outside a weight ratio of about 7:13 to about 13:7, the resultant reaction media will generally fail to provide the desired stabilizing thermoset viscoelastomer having an adhesion release strength of more than 300 $g_f/cm^2$.

An effective stabilizing thermoset viscoelastomeric polymerizate overlay 5 characteristically possesses a capacity to adhesively restrain the cosmetic item 13 at a desired stabilized position upon an appropriate supportive base 3 while also allowing for an effective release of a cosmetic item 13 therefrom upon an application of an outwardly counteracting force sufficient to overcome the adhesive force binding the cosmetic item 13 to the overlay 5. The stabilizing overlay 5 also possesses a tenacious internal compositional adhesiveness as evidenced by its ability to break cleanly away from its adhesive bonding to the cosmetic item 13. Characteristically, upon adhesive separation, the overlay 5 will remain substantially intact in its innate form with no more than a minuscule level of stabilizing overlay 5 adhering to the separated cosmetic item 13. Upon separation, there will accordingly exist no visible evidence of overlay residue upon the cosmetic item 13, with the overlay 5 readily returning to its innate form after separation.

The resultant cross-linked polymeric structure of the thermoset polymerizate obtained from an appropriate thermoset reaction media provides an ideal infrastructure for effectively harboring plasticizer components in an unexpectedly superior cohesive and adhesive form. The plasticizer is uniformly incorporated into the reaction media (containing the polymerizable thermosetting components) and remains uniformly dispersed within the resultant thermoset reaction product in a highly adhesive and stabilized form. Typically, the amount of plasticizer will range from about 20% to about 55% by weight of the total reaction media weight with the plasticizer being uniformly and adhesively dispersed throughout the reaction media and the resultant thermoset viscoelastomer derived therefrom. Most typically, the thermosetting reaction media for the most effective overlays 5 will contain from about 20% to about 48% by weight plasticizer with the plasticizer content constituting from 0% to about 48% by weight of a triglyceride plasticizer (e.g., an epoxidized triglyceride) and from about 0% to about 40% by weight of an ester plasticizer, typically as a di-ester plasticizer. The thermosetting diols and triols, in cooperative combination with the plasticizer, create a thermoset viscoelastomeric polymeric structure possessing the high degree of compositional adhesiveness necessary to adhesively secure and retain the cosmetic item 13 to the overlay 5, while also allowing for a clean cohesive separation from the cosmetic item 13. Thus, the type of plasticizer and reactants, in monitored amounts, can be effectively utilized to provide the desirable thermosetting fabricating conditions, as well as the ultimate reaction product and overlay 5 attributes.

The diol may typically be provided by a polyether diol having a molecular weight ranging from about 2,000 to about 6,000 in an amount ranging from about 10% to about 20% by weight of the reaction media weight. The diol provides sufficient cross-linkage disruption and straight chain infrastructure to permit a highly effective loading of the viscoelastomeric thermoset with a cohesive and adhesive plasticizer co-factor. The triol may typically be provided by a polyether triol (typically having a molecular weight ranging from about 3,000 to about 7,000) in an amount ranging from about 25% to about 35% by weight. The reaction media also suitably includes a polyurethane precursor in an amount of about 4% to about 7% by weight (e.g., di-isocyanate prepolymer) and from about 20% to about 48% by weight plasticizer adhesively bound within the thermoset reaction infrastructure, which may be formulated so as to suitably provide a thermoset viscoelastomeric reaction product overlay having an adhesion release strength of at least 400 $g_f/cm^2$.

Although the stabilizing viscoelastomeric thermoset overlay 5 will generally possess unexpectedly superior adhesiveness, the stabilizing overlay 5 will also possesses unexpectedly superior releasable cohesive attributes. For example, upon exposure to a separating adhesive release force (e.g., such as pulling the cosmetic item 13 away from the overlay's adhesive engagement), the compositional cohesiveness of the viscoelastomeric thermoset overlay 5 tenaciously retains its structural integrity by separating cleanly from the cosmetic item 13 without leaving more than a trace of compositional residue upon the separated cosmetic item 13. As the overlay tack level increases, there arises a cohesive and adhesive tendency of the overlay 5 to pull away from the adhesively engaged cosmetic item 13 in a taffy-like manner until the stabilizing overlay 5 completely separates or breaks cleanly away from the adhered cosmetic item 13. The stretched portion of the overlay 5 readily cohesively returns to its innate overlay form. The overall tackiness (i.e., adhesiveness) and cohesiveness of the viscoelastomeric thermoset stabilizing overlay 5 and its concomitant releaseability characteristics may be altered by the compositional makeup of the thermosetting reaction media, particularly by the diol to triol weight ratio of the reaction media, as well as the reaction media plasticizer content and type of plasticizer. Thus, the cohesive and adhesive attributes of the thermoset viscoelastomeric stabilizing overlay 5 may be tailored to meet the desired level of adhesiveness for general use or for a particular cosmetic item 13. An effective manner of regulating the adhesion release strength involves altering the diol to triol weight ratio in the thermosetting reaction media.

In general, the adhesion release strength (i.e., tackiness) will decrease as the triol reactant weight increases, and will increase as the diol reactant weight increases. In order to compensate for an increase of the diol reactant weight in the reaction media, a slight increase in the di-isocyanate reactant amount will generally balance the reaction media reactants. Surprisingly, the adhesiveness of the stabilizing overlay 5 is maintained throughout an adhesion release strength range of at least 300 $g_f/cm^2$ to 900 $g_f/cm^2$. Typically, the higher adhesion release strength values will tend to tenaciously string out similar to the pulling of heated candy taffy until a clean adhesive separation ultimately occurs, whereupon the overlay 5 returns to its innate form. The high tack levels are prone to make it more difficult for the cosmetic user to effectively release the cosmetic item 13 from the stabilizing overlay 5, especially at an adhesion release strength level of more than 900 $g_f/cm^2$. Most cosmetic users desire a cosmetic combination allowing for the ease of a one-handed cosmetic item 13 removal from the overlay 5 (e.g., an adhesion release strength of about 400 to about 700 $g_f/cm^2$), which becomes more difficult at relatively higher adhesion release strength levels.

The viscoelastomeric stabilizing overlay 5 may be provided as a preformed insert. The preformed insertable overlay 5 may be adhesively inserted as an adhesive inlay 5 to the tray bed 3B. Due to the exceptional adhesive qualities of the viscoelastomeric thermoset, the overlay 5 may be provided in a film, sheet, insert etc. form which, due to its tack, will tenaciously adhere to conventional cosmetic tray beds 3B until a counteracting force causes its removal. Alternatively, the reaction product may be directly bonded in situ to the cosmetic tray bed 3B by applying a flowable uncured thermosetting reaction media of the reactants to the bed 3B, and thereafter allowing the reaction media to cure in situ to provide a thermoset viscoelastomeric overlay 5 bonded by thermosetting to the bed 3B.

Irrespective of how the overlay 5 is bonded to the cosmetic bed 3B, the viscosity characteristics of uncured thermosetting reaction media of the cured polymerizate may be effectively tailored so as to provide a workable viscosity for effectively forming the thermoset overlay 5. The thermosetting reaction media for preparing the thermoset viscoelastomer overlay 5 may accordingly be characteristically formulated to possess film-forming, coating, molding, etc. properties during the initial thermosetting lower viscosity stages of the viscoelastomeric thermosetting reaction. The viscosity of the thermosetting reaction media may be accordingly suitably formulated so as to possess a sufficient fluidity to allow for the coatings, filming or other molding processes to be conducted under conventional thermoset molding, casting, etc. techniques. Procedurally, a measured amount of the fluid thermosetting reaction media may be deposited or casted upon an cosmetic tray bed 3B, allowed to spread evenly (due to a desirable casting viscosity) and then cured in situ to provide the desired overlaying member 5 tenaciously bonded to the tray bed 3B. Controlling the initial viscosity properties of the thermosetting reaction media provides a convenient manufacturing procedure for preparing a cosmetic tray 1 equipped with the thermoset stabilizing overlay 5 bonded thereto. Thus, conventional calendaring, casting, molding, coating, etc. thermosetting film-forming techniques may be effectively used to prepare the overlay 5 in either a coated thermoset or insert form at a workable viscosity range.

By adjusting the plasticizer content and type, the characteristics of the reaction media (including the ultimate thermoset tack, as well as the initial reaction media thermosetting viscosity characteristics) may be effectively altered so as to suit a particular type of manufacture. For example, effective casted coating manufacture procedurally typically requires a workable viscosity so that a desired coating or film may be produced. This generally entails pouring, injecting, casting, etc. the thermosetting reaction media at a workable viscosity onto a supportive substance to provide a uniformly casted coating, film, sheet, etc. Particularly suitable for this purpose is formulating the reaction media with an effective amount of viscosity reducing di-ester plasticizers, especially the di-alkyl esters of di-carboxylic acids, which generally impart sufficient onset fluidity reduction so as to provide a thermosetting reaction media which may be easily poured, molded or casted during its initial thermosetting stages.

Characteristically, these di-alkyl ester plasticizers are fluid at room temperature (e.g., 20° C.) and have a molecular weight of less than 500. Exemplary thereof are the condensation products of alcohols (e.g., $C_1$ to $C_{10}$ alcohols) and $C_2$-$C_{12}$ dicarboxylic acids, particularly the condensates of $C_2$ to $C_6$ alcohols and $C_4$-$C_8$ dicarboxylic acids. Typically, the total plasticizer concentration will most suitably range from about 20% to about 45% by weight of the reaction media weight, and most typically will range from about 25% to about 40% by weight. The weight ratio of epoxidized triglyceride plasticizer to non-epoxidized plasticizer (e.g., di-esters) within the reacting media will typically range from about 1:0 to about 1:3, and most typically from about 1:1 to about 3:1, especially under those thermosetting conditions wherein the di-ester plasticizers are used to prepare the stabilizing overlay 5.

Since it is desirable for most manufacturing applications to use a more fluid thermosetting reaction media, the more fluid di-ester plasticizers are particularly effective for this purpose. The enhanced fluidity characteristics become particularly useful in casting procedures, such as the casting of thin films or coatings upon the cosmetic tray bed 3B. Such thermosetting casting techniques also tend to create a tenacious bonding between the cured stabilizing overlay 5 and the tray bed 3B. Amongst the more fluid di-ester plasticizers are lower di-alkyl esters of di-carboxylic acids. Exemplary thereof are di-alkyl esters having alkyl groupings of less than 12 carbon atoms, and more typically of $C_1$ to $C_8$ di-alkyl ester groupings of sebacates, adipates, phthalates, isophthalates, maleates, azelates, glutarates, etc. The total plasticizer concentration in such casting manufacturing techniques will most suitably range from about 20% to about 45% by weight, and most typically range from about 25% to about 40% by weight, with the weight ratio of epoxidized triglyceride to non-epoxidized plasticizer (e.g., di-esters) typically ranging from about 1:0 to about 1:3, and most typically from about 1:1 to about 3:1. Due to its availability, and the excellent resultant reaction media viscosity and end product characteristics, dibulyl sebacate has been found to be an effective di-alkyl ester plasticizer. A balanced proportion of triglyceride plasticizer and di-alkyl ester plasticizer (e.g., about 1:1 to about 1:0) has generally been found to provide useful attributes in providing a desired thermosetting viscosity and reaction product (i.e., stabilizing overlay 5). On a reaction media weight basis, the di-alkyl ester plasticizer content for casting purposes may desirably range from about 1% to about 20% by weight, and most typically from about 5% to about 15% by weight of the total reaction media weight.

When effectively used as a stabilizing overlay 5 bonded to the cosmetic tray bed 3B, the overlay 5 will restrain the cosmetic item 13 at a desirable preset position. The cosmetic item 13 will steadfastly maintain its emplaced position without undesirable movement notwithstanding being subsequently exposed to relatively powerful disruptive external force. Consequently, abruptly dropping or jarring the cosmetic tray combination 1 will typically fail to dislodge the cosmetic item 13 from its restrained mooring to the stabilizing overlay 5. In contrast to conventional cosmetic trays notoriously known for a propensity to scatter trayed cosmetic items 13 when abruptly dislodged, the cosmetic combination 1 as provided by this invention will tenaciously restrain a seated cosmetic item 13 to its original emplaced seating under the most rigorous abusive conditions. Thus, an abrupt movement of the cosmetic combination 1 equipped with the stabilizing overlay 5 will restrain and protect the cosmetic item 13 from dislodgement. These exceptional stabilizing effects are accomplished while still providing an ease for emplacement and removal of the cosmetic item 13 upon the cosmetic tray 1.

The stabilized cosmetic tray 1 may be conveniently provided with a movable handle 9 and covering lid 11 which may be easily displaced to provide tray access. Thus, the movable handle 9 and covering lid 11 may be designed to be taken off or moved away from their original occupied position to provide for cosmetic tray display and access. The covering lid 11 and handle 9 may be hinged, detachable or otherwise movably mounted for repositioning from their covering or hand carrying positions, respectively.

EXAMPLE

A thermosetting reaction media suitably formulated to serve as a casted overlay 5 upon a conventional cosmetic display tray bed 3B and possessing excellent casting viscosity characteristics was prepared from a uniform admixture of the following thermosetting reactants:

|  | Percent by Weight: |
| --- | --- |
| A-Mix Ingredients: | |
| Methylene diphenyl diisocyanate based glycol prepolymer (ElastoCAST TQZP23, available from BASF Corporation) | 6.46% |
| Epoxidized soybean oil | 26.88% |
| Dibutyl sebacate | 8.96% |
| B-Mix Ingredients: | |
| Polyether triol (ElastoCAST C-4018, available from BASF Corporation) | 26.88% |
| Polyether diol (ElastoCAST C-4057, available from BASF Corporation) | 29.32% |
| Catalyst (COSCAT 83, available from Vertellus Specialties) | 0.16% |
| UV inhibitor (TINUVIN B75) | 1.30% |
| Colorant blend (1:1) | 0.04% |
| Total | 100% |

During the initial thermosetting stages, a bed 3B of a conventional high density polypropylene cosmetic tray 1 of the type illustrated by the Figures was uniformly coated with a 100 mil thick coating of the aforementioned reaction media by casting measured amounts thereof onto the cosmetic tray bed 3B. The container bed 3B had been preflamed to permit a more effective bonding of the stabilizing overlay 5 thereto. The casted overlay coating was allowed to fully cure to provide a thermoset viscoelastomeric stabilizing overlay 5 characterized as having an average adhesion release strength of 800 g/cm² (wherein the average was derived from 10 tested samples).

A number of conventional cosmetic items 13 (e.g., cologne, perfume, lipstick, eyeliner, deodorant, etc. containers; razor blades; tweezers; nail clippers; etc.) were then placed upon the tray 1 equipped with the casted thermoset reaction product overlay 5. Notwithstanding strenuous abusive mishandling, the emplaced cosmetic items 13 maintained their original placement position upon the display bed overlay 5. Similar results were achieved upon toting the cosmetic-loaded combination 1 under rigorous toting conditions. The adhesion release strength value of the casted overlay 5 permitted the cosmetic user to easily, with a single hand, remove a desired cosmetic item 13 from the overlay 5. This was accomplished without lifting the whole tray combination 1 when removing a particular cosmetic item 13 therefrom.

What is claimed is:

1. A cosmetic tray equipped to restrain an emplaced cosmetic item at a stowable position until manually removed therefrom, said cosmetic tray comprising a supportive base for supporting cosmetic items placed thereupon and a cohesive and adhesive stabilizing thermoset polymerizate overlay characterized as having an adhesion release strength of at least 300 g/cm² overlaying the supportive base.

2. The cosmetic tray according to claim 1 wherein the polymerizate overlay is prepared from a thermosetting reaction media comprised of a substantially uniform admixture of an isocyanate precursor, an effective amount of plasticizer containing less than 50 percent by weight of the reaction media of an epoxidized triglyceride plasticizer, from about 35 to about 55 percent by weight of the reaction media polyols with said polyols consisting essentially of a straight chain linking diol and a cross-linking polyol each of which contain repetitive oxy groups at a diol to polyol weight ratio ranging from about 1:2 to about 2:1 in combination with a sufficient amount of plasticizer to provide an adhesion release strength of more than 400 grams force per centimeter square.

3. The cosmetic tray according to claim 2 wherein the supportive base comprises a tray bed equipped with confining sidewalls and a removable lid.

4. The cosmetic tray according to claim 3 wherein the overlay comprises an insertable overlay having an adhesion release strength ranging from about 400 to about 900 g/cm² adhesively bonded to the bed.

5. The cosmetic tray according to claim 3 wherein the overlay comprises an overlaying thermoset coating obtained by thermosetting the reaction media to the bed with the overlay being characterized as having an adhesion release strength ranging from about 500 to about 800 g/cm².

6. The cosmetic tray according to claim 1 wherein the supportive base comprises a bed of a cosmetic tray container equipped with confining sidewalls, a removable covering lid and a toting handle.

7. The cosmetic tray according to claim 6 wherein the overlay comprises a viscoelastomeric thermoset coating having an adhesion release strength ranging from at least 400 g/cm² to about 900 g/cm² bonded to the bed by the thermosetting thereto of a reaction media which forms the viscoelastomeric thermoset coating.

8. The cosmetic tray according to claim 7 wherein the tray includes a plurality of the cosmetic items adhesively engaging the overlay.

9. The cosmetic tray according to claim 1 wherein a thermosetting reaction media for preparing the thermoset polymerizate overlay comprises:

a. from about 4% to 7% by weight of the reaction media of an di-isocyanate prepolymer;
 b. from about 25% to about 35% by weight of the reaction media of a polyether triol as the cross-linking triol;
 c. a straight chain producing polyether diol in an amount ranging from about 10% to about 35% by weight of the reaction media with the weight ratio of the polyether diol to the polyether triol provided in the reaction media ranging from about 7:13 to about 13:7 and
 d. about 20% to 55% by weight of the reaction media of plasticizer uniformly dispersed within the reaction media with the reaction media containing less than 50% by weight of the reaction media of epoxidized triglyceride and from 0% to about 40% by weight of the reaction media of di-ester plasticizer.

10. The cosmetic tray according to claim 9 wherein the epoxidized triglyceride comprises from about 35% to about 48% by weight of the total reaction media weight and the weight ratio of straight linking diols to cross-linking triols ranges from about 2:3 to about 3:2.

11. The cosmetic tray according to claim 9 wherein the reaction media contains on a total plasticizer weight basis from about 25% to about 50% by weight of the di-ester plasticizer.

12. The cosmetic tray according to claim 11 wherein the di-ester plasticizer comprises dibutyl sebecate.

13. The cosmetic tray according to claim 11 wherein the polyether triol comprises a polyoxyalkylene of a molecular weight ranging from about 3,000 to about 7,000 selected from the group consisting of polyoxyethylene triol and polyoxypropylene triol.

14. The cosmetic tray according to claim 13 wherein the polyether diol has a molecular weight ranging from about 2,000 to about 6,000 and is selected from the group consisting polyoxyethylene diol and polyoxypropylene diol.

15. The cosmetic tray according to claim 14 wherein the supportive base comprises a bed of a cosmetic display tray equipped with confining sidewalls and a removable covering lid.

16. The cosmetic tray according to claim 15 wherein the cosmetic tray includes a carrying handle.

17. The cosmetic tray according to claim 16 wherein the tray contains adhesively restrained cosmetic items.

18. The cosmetic tray according to claim 16 wherein the adhesion separation strength of the overlay ranges from about 400 g/cm² to about 700 g/cm².

19. The cosmetic tray according to claim 18 wherein the overlay comprises a detachable adhesive overlaying insert adhesively affixed to the bed.

20. The cosmetic tray according to claim 18 wherein the stabilizing overlay comprises a thermoset viscoelastomeric coating bonded to the bed.

21. A method for manufacturing a cosmetic tray adapted to restrain cosmetic items emplaced within the tray, said method comprising:

a. providing a cosmetic tray equipped with a supportive base;
 b. preparing an cohesive and adhesive thermoset elastomeric overlay having a cured adhesion release strength of at least 300 g/cm² and a cohesive capacity to cleanly release from the cosmetic items without leaving more than a minuscule amount of residue upon release therefrom; and
 c. applying the overlay or a thermosetting precursor of the overlay to the supportive base to provide the cohesive and adhesive elastomeric overlay possessing sufficient adhesiveness to restrain the cosmetic items thereupon.

22. The method according to claim 21 wherein the preparing of the overlay comprises uniformly admixing together a thermosetting reaction media comprised of:
 a. from about 4% to 7% by weight of the reaction media of a di-isocyanate prepolymer;
 b. from about 10% to 35% by weight of the reaction media of a polyether diol;
 c. from about 25% to about 35% by weight of the reaction media of a polyether triol with the weight ratio of diol to triol ranging from about 7:13 to about 13:7; and
 d. a sufficient amount of plasticizer to provide an adhesion release strength of more than 400 $g_f/cm^2$.

23. A cosmetic container combination having a supportive base which is supportive of cosmetic items placed thereupon, comprising a cohesive and adhesive thermoset viscoelastomeric overlay disposed upon the supportive base, wherein the overlay has sufficient adhesiveness to restrain the cosmetic items placed thereupon at a desired stabilized position while also allowing for a release of the cosmetic items from the overlay by applying a sufficient counteracting manual force to separate the cosmetic items from the overlay with the overlay being further characterized as cohesively separating from the cosmetic items while leaving no more than trace amounts of the overlay upon the cosmetic items separated therefrom while the overlay remains firmly bonded to the supportive base upon the separation of the cosmetic items therefrom.

24. The cosmetic container combination according to claim 23 wherein the overlay consists essentially of a thermoset viscoelastomeric polymerizate.

25. The cosmetic container combination according to claim 24 wherein the overlay is characterized as having an adhesion release strength ranging from at least 300 $g_f/cm^2$ to about 800 $g_f/cm^2$.

26. The cosmetic container combination according to claim 25 wherein the container comprises a tray bed as the supportive base with the overlay having an outer exposed adhesive surface for interfacial engagement onto the cosmetic items.

27. The cosmetic container combination according to claim 26 wherein the combination comprises a hand carryable cosmetic display tray equipped with side rails enclosing the bed, a removable covering lid and a toting handle.

28. A method of retrofitting a conventional cosmetic tray, said method comprising:
 a. providing a cohesive and adhesive viscoelastomeric insertable overlay sized to mate onto a supportive bed of the cosmetic tray with said insertable overlay being characterized as having an adhesion release strength of at least 300 $g_f/cm^2$ and sufficient cohesiveness so as to remain substantially intact upon an adhesive release of the overlay from the supportive bed and
 b. inserting the overlay onto the supportive bed so as to provide a cosmetic container adapted to adhesively restrain cosmetic items emplaced thereupon.

29. The method according to claim 28 wherein the insertable overlay comprises a thermoset viscoelastomeric polymerizate.

30. The method according to claim 29 wherein the providing includes protectively covering the insertable overlay with a temporary peelable thermoplastic film, a subsequent removing of the thermoplastic film from the insertable overlay followed by the inserting of the insertable overlay onto the supportive bed.

31. The method according to claim 29 wherein the thermoset viscoelastomeric polymerizate consists essentially of the thermoset reaction product of a reaction media comprised of:
 a. from about 4% to 7% by weight of the reaction media of a di-isocyanate prepolymer;
 b. from about 10% to 35% by weight of the reaction media of a polyether diol;
 c. from about 25% to about 35% by weight of the reaction media of a polyether triol with the weight ratio of diol to triol ranging from about 7:13 to about 13:7; and
 d. a sufficient amount of plasticizer to provide an adhesion release strength of more than 400 $g_f/cm^2$ and less than 750 $g_f/cm^2$.

32. The method according to claim 31 wherein the polyether diol comprises a member selected from the group consisting of polyoxyethylene diol and polyoxypropylene diol having a molecular weight ranging from about 2,000 to about 6,000 and the polyether triol comprises a member selected from the group consisting of polyoxyethylene triol and polyoxypropylene triol having a molecular weight ranging from about 3,000 to about 7,000.

33. The method according to claim 32 wherein the weight ratio of diol to triol ranges from 2:3 to 3:2.

34. The method according to claim 33 wherein the adhesion release strength ranges from about 400 $g_f/cm^2$ to about 700 $g_f/cm^2$.

* * * * *